United States Patent
Giffey et al.

(10) Patent No.: US 9,414,896 B2
(45) Date of Patent: Aug. 16, 2016

(54) METHODS AND MATERIALS FOR ORAL STENTING

(71) Applicant: Mayo Foundation for Medical Education and Research, Rochester, MN (US)

(72) Inventors: Broc T. Giffey, Rochester, MN (US); Robert L. Foote, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/749,963

(22) Filed: Jun. 25, 2015

(65) Prior Publication Data
US 2015/0289948 A1 Oct. 15, 2015

Related U.S. Application Data

(63) Continuation of application No. 13/180,231, filed on Jul. 11, 2011, now abandoned.

(60) Provisional application No. 61/365,086, filed on Jul. 16, 2010.

(51) Int. Cl.
| | |
|---|---|
| *A61C 5/14* | (2006.01) |
| *A61B 1/24* | (2006.01) |
| *A61B 13/00* | (2006.01) |
| *A61N 5/10* | (2006.01) |
| *A61B 17/24* | (2006.01) |
| *A61B 17/00* | (2006.01) |

(52) U.S. Cl.
CPC ... *A61C 5/14* (2013.01); *A61B 1/24* (2013.01); *A61B 13/00* (2013.01); *A61B 90/16* (2016.02); *A61N 5/1001* (2013.01); *A61B 17/24* (2013.01); *A61B 2017/00955* (2013.01); *A61N 2005/1094* (2013.01)

(58) Field of Classification Search
CPC ............... A63B 2071/088; A63B 2208/12; A63B 71/085; A61B 18/1492; A61C 7/08; A61C 5/12; A61C 7/00; A61C 19/003; A61C 3/00; A61C 3/06; A61C 5/127; A61C 5/125; A61F 2/00; A61F 2/20; A61F 2005/563; A61F 5/56; A61F 5/566
See application file for complete search history.

(56) References Cited

U.S. PATENT DOCUMENTS

| | | | |
|---|---|---|---|
| 5,190,990 A | 3/1993 | Eichmiller | |
| 5,550,383 A | 8/1996 | Haskell | |
| 5,775,900 A | 7/1998 | Ginsburg et al. | |
| 6,450,167 B1 | 9/2002 | David et al. | |
| 6,467,484 B1* | 10/2002 | De Voss | A61F 5/566 128/848 |
| 8,312,884 B2 | 11/2012 | Fuselier | |
| 2003/0224313 A1 | 12/2003 | Bergersen | |
| 2005/0175954 A1* | 8/2005 | Zacher | A61F 5/566 433/5 |
| 2009/0038624 A1 | 2/2009 | Akervall et al. | |
| 2009/0050161 A1 | 2/2009 | Burdumy | |
| 2009/0130624 A1 | 5/2009 | Sun et al. | |
| 2010/0108078 A1 | 5/2010 | Morgan et al. | |
| 2012/0012120 A1 | 1/2012 | Giffey et al. | |

OTHER PUBLICATIONS

Bodard et al., "A new, simple maxillary-sparing tongue depressor for external mandibular radiotherapy: a case report," Head Neck, 31(11):1528-1530, Nov. 2009.

* cited by examiner

*Primary Examiner* — Ophelia A Hawthorne
(74) *Attorney, Agent, or Firm* — Fish & Richardson P.C.

(57) ABSTRACT

This document provides methods and materials related to oral stenting. For example, oral stenting devices (e.g., adjustable oral stenting devices) and methods for using oral stenting devices for radiation therapy are provided.

10 Claims, 8 Drawing Sheets

METHODS AND MATERIALS FOR ORAL STENTING

CROSS-REFERENCE TO RELATED APPLICATIONS

This application is a continuation of U.S. application Ser. No. 13/180,231, filed Jul. 11, 2011, which claims the benefit of U.S. Provisional Application Ser. No. 61/365,086, filed Jul. 16, 2010. The disclosure of the prior applications are considered part of (and are incorporated by reference in) the disclosure of this application.

BACKGROUND

1. Technical Field

This document relates to methods and materials for oral stenting. For example, this document provides oral stenting devices and methods for using oral stenting devices for radiation therapy.

2. Background Information

During radiotherapy of head and neck cancers, healthy tissues can suffer from radiation damage. In some cases, acute mucosal reactions may limit the rate of treatment or cause unplanned interruption, and soft tissue or bone necrosis may limit the total radiation dose that can be delivered, thereby potentially compromising treatment efficacy.

SUMMARY

This document provides methods and materials related to oral stenting. For example, this document provides oral stenting devices and methods for using oral stenting devices for radiation therapy. In some cases, the oral stenting devices provided herein can be adjustable. Such adjustable oral stenting devices can be used in radiotherapy of head and neck cancers. As described herein, an adjustable intraoral stenting device provided herein can be used to shield healthy tissue and stabilize the mouth and tongue during head and neck radiotherapy.

In general, one aspect of this document features an oral stenting device comprising, or consisting essentially of, an upper tray, a lower tray, and an actuator, wherein the actuator is operable to change the angular relationship between the upper tray and the lower tray. The actuator can comprise a ratcheting mechanism. The oral stenting device can comprise a base member. The base member can comprise a thermoplastic material. The oral stenting device can comprise a tongue depressor. The oral stenting device can comprise a thermoplastic material.

In general, one aspect of this application features an oral stenting device comprising, or consisting essentially of, an upper tray, a lower tray, and an actuator, wherein the actuator is operable to change the angular relationship between the upper tray and the lower tray. The actuator can comprise a ratcheting mechanism. The oral stenting device can further comprise a base member. The base member can comprise a thermoplastic material. The oral stenting device can further comprise a tongue depressor. The oral stenting device can comprise a thermoplastic material. The oral stenting device can comprise a teeth guard structure that extends upward from the upper tray along an outside edge of the upper tray. The oral stenting device can comprise a teeth guard structure that extends downward from the lower tray along an outside edge of the lower tray. The oral stenting device can comprise an upper teeth guard structure that extends upward from the upper tray along an outside edge of the upper tray and a lower teeth guard structure that extends downward from the lower tray along an outside edge of the lower tray.

In another aspect, this document features an oral stenting device comprising, or consisting essentially of, an upper tray, a lower tray, and a removable wedge structure or removable screw device, wherein insertion of the removable wedge structure or removable screw device into the oral stenting device between the upper tray and the lower tray changes the angular relationship between the upper tray and the lower tray. The oral stenting device can comprise the removable wedge structure. The oral stenting device can comprise the removable screw device. The oral stenting device can further comprise a base member. The base member can comprise a thermoplastic material. The oral stenting device can further comprise a tongue depressor. The oral stenting device can comprise a thermoplastic material. The oral stenting device can comprise a teeth guard structure that extends upward from the upper tray along an outside edge of the upper tray. The oral stenting device can comprise a teeth guard structure that extends downward from the lower tray along an outside edge of the lower tray. The oral stenting device can comprise an upper teeth guard structure that extends upward from the upper tray along an outside edge of the upper tray and a lower teeth guard structure that extends downward from the lower tray along an outside edge of the lower tray.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

This document provides methods and materials related to oral stenting. For example, this document provides oral stenting devices and methods for using oral stenting devices for radiation therapy. An oral stenting device provided herein can be adjustable. Such an adjustable oral stenting device can be configured to open a patient's mouth (e.g., a human patient's mouth) gradually and in a manner that is comfortable for the patient. As described herein, the oral stenting devices provided herein can be used to shield healthy tissue and stabilize the mouth and tongue during head and neck radiotherapy. In some cases, an oral stenting device provided herein can be configured to depress the tongue out of the radiation field. For example, an oral stenting device provided herein can include a tongue depressor.

The methods and materials provided herein can be used by any appropriate patient. For example, patients with cancer (e.g., primary cancer) of the oral cavity, nasal cavity, oropharynx, paranasal sinuses, tongue, palate, and salivary glands can use an oral stenting device provided herein. In some cases, the methods and materials provided herein can be used during an oral surgery or during orthodontics or dentistry procedures.

With reference to FIGS. 1A-B and FIGS. 1C-D, oral stenting device 10 can be configured to include an upper tray 12 and a lower tray 14. Oral stenting device 10 can have a generally arcuate shape conforming to the general shape of a user's jaw to receive substantially all of the user's upper teeth and lower teeth. In some cases, an oral stenting device provided herein can have other shapes and sizes. For example, an oral stenting device, an upper tray of an oral stenting device, and/or a lower tray of an oral stenting device can have a shape and size such that they conform with all or only a portion of the user's teeth (e.g., two, three, four, five, six, seven, eight, or more of the user's teeth). In some cases, oral stenting devices provide herein can be configured such that the lower tray conforms with all the user's lower teeth, while the upper tray conforms with a portion of the user's upper teeth (e.g., two, three, four, five, six, seven, or eight of the user's upper teeth). In some cases, an oral stenting device provide herein can be configured such that the upper tray conforms with all the user's upper teeth, while the lower tray conforms with a portion of the user's lower teeth (e.g., two, three, four, five, six, seven, or eight of the user's lower teeth).

Figure 1A:
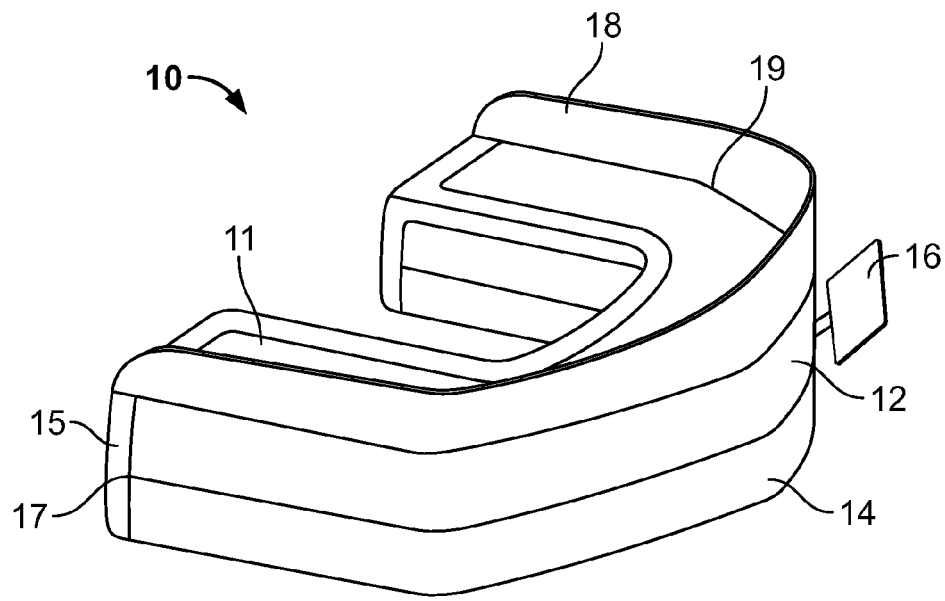
FIGS. 1A-D are prospective views of an oral stent device in a closed position (FIGS. 1A and C) and an open position (FIGS. 1B and D), in accordance with some embodiments.
Figure 1B:
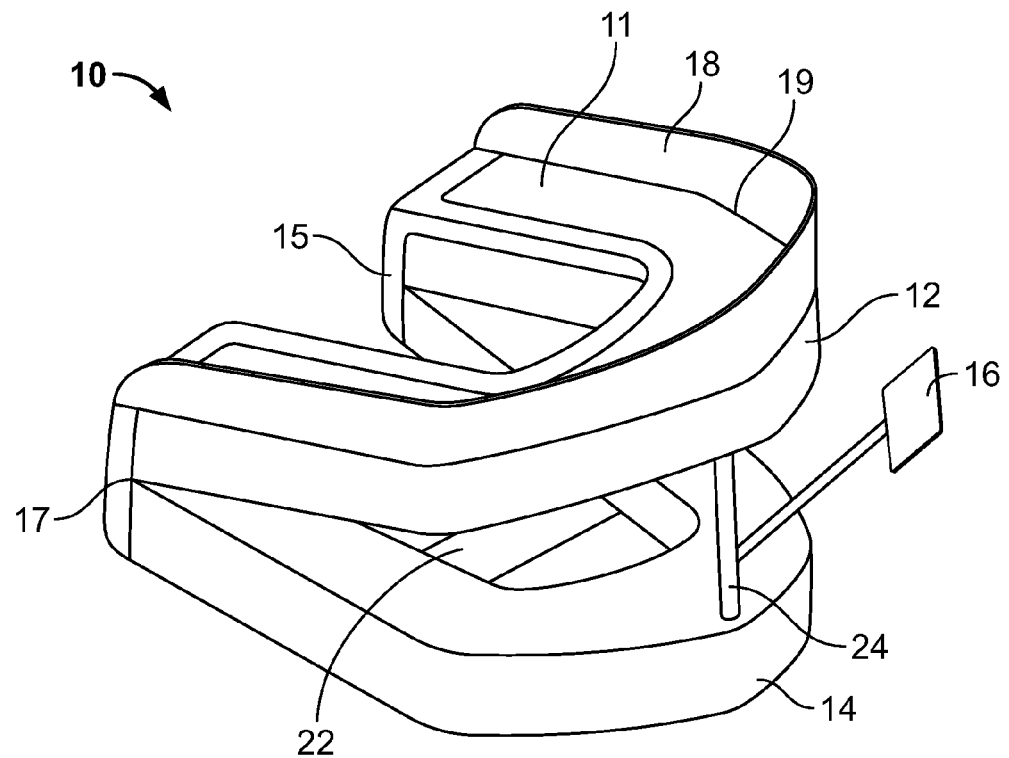

With further reference to FIGS. 1A-B, upper tray 12 of oral stenting device 10 can be configured to include a teeth guard 18 and a base member 11. Teeth guard 18 can be configured to extend from an outside edge 19 of base member 11 along the front face of a user's upper teeth when the oral stenting device is positioned within the user's mouth. In some cases, a teeth guard can be configured to extend from an inside edge of a base member along the inside face of a user's upper teeth when the oral stenting device is positioned within the user's mouth. In some cases, a teeth guard can be configured to extend from both an outside edge and an inside edge of a base member along both the front face and inside face of a user's upper teeth when the oral stenting device is positioned within the user's mouth.

In some cases, base member 11 can include a distal end 15 that extends from a top surface of upper tray 12 to a lower surface of lower tray 14. As shown in FIGS. 1A-B and FIGS. 1C-D, distal end 15 of base member 11 can connect upper tray 12 to lower tray 14. In some cases, upper tray 12 and lower tray 14 can be attached via a spring element.

Figure 1C:
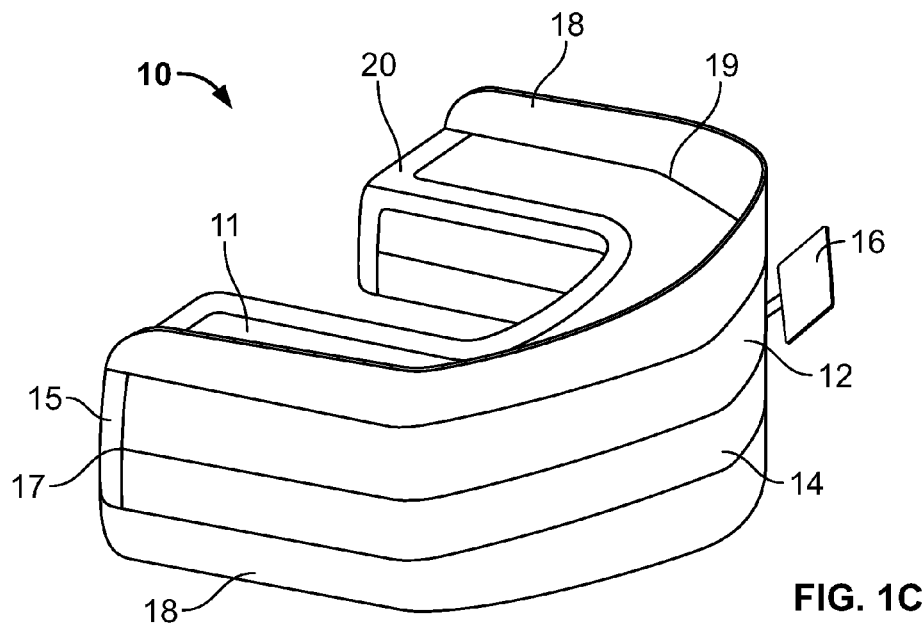
Figure 1D:
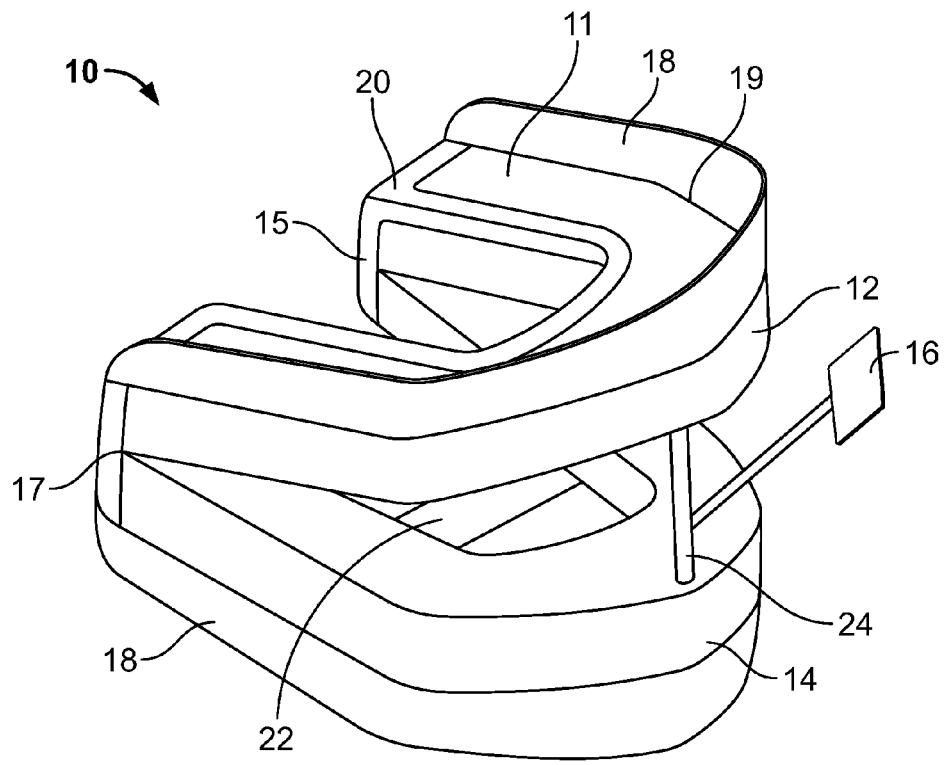

In some embodiments, upper tray 12 and lower tray 14 of an oral stenting device can be configured to include a teeth guard 18 and a base member 11 as shown in FIGS. 1C-D. In such cases, base member 11 of upper tray 12 can be configured to engage the bottom surface of the user's upper teeth, and base member 11 of lower tray 14 can be configured to engage the top surface of the user's lower teeth.

With further reference to FIGS. 1A-B and FIGS. 1C-D, upper tray 12 and lower tray 14 can be configured to be connected to each other via, for example, a hinge arrangement 17. Hinge arrangement 17 can be formed by the connection of upper tray 12 to lower tray 14 via distal end 15. As oral stenting device 10 is opened from a closed position about hinge arrangement 17, distal end 15 can flex to accommodate the opening motion. For example, base member 11 can be composed of a flexible material that can allow opening and closing of oral stenting device 10.

With further reference to FIGS. 1A-B and FIGS. 1C-D, oral stenting device 10 can be configured to include an actuator 16. Actuator 16 can be configured to move upper tray 12 and lower tray 14 apart from one another when actuated. In some cases, actuator 16 can be configured to include a mechanism 24. Mechanism 24 can be a ratcheting mechanism, a dial mechanism, a screw mechanism, a lever mechanism, a spring mechanism, a scissor jack mechanism, a telescoping mechanism, or combination thereof that is designed to selectively open stenting device 10 or separate upper tray 12 from lower tray 14.

Figure 2A:
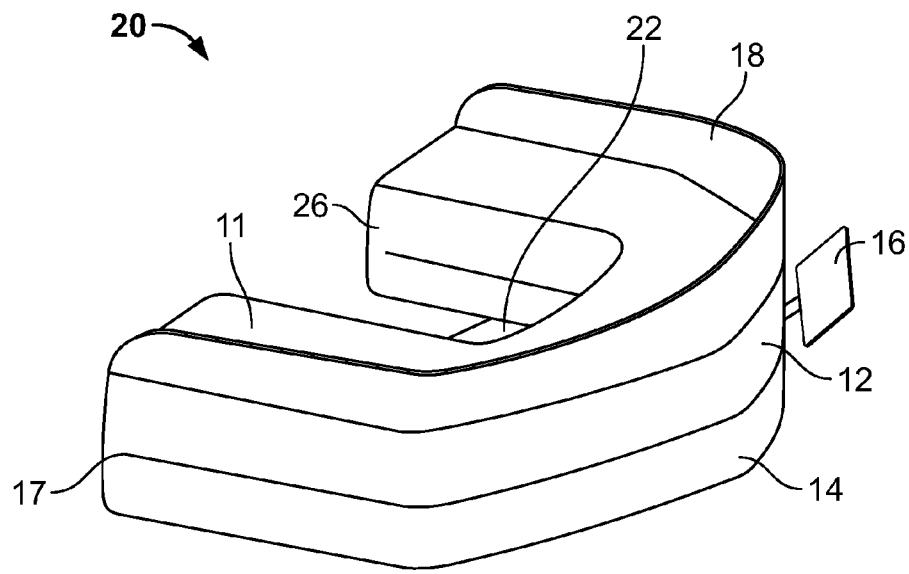
FIGS. 2A-B are prospective views of an oral stent device in a closed position (FIG. 2A) and an open position (FIG. 2B), in accordance with some embodiments.
Figure 2B:
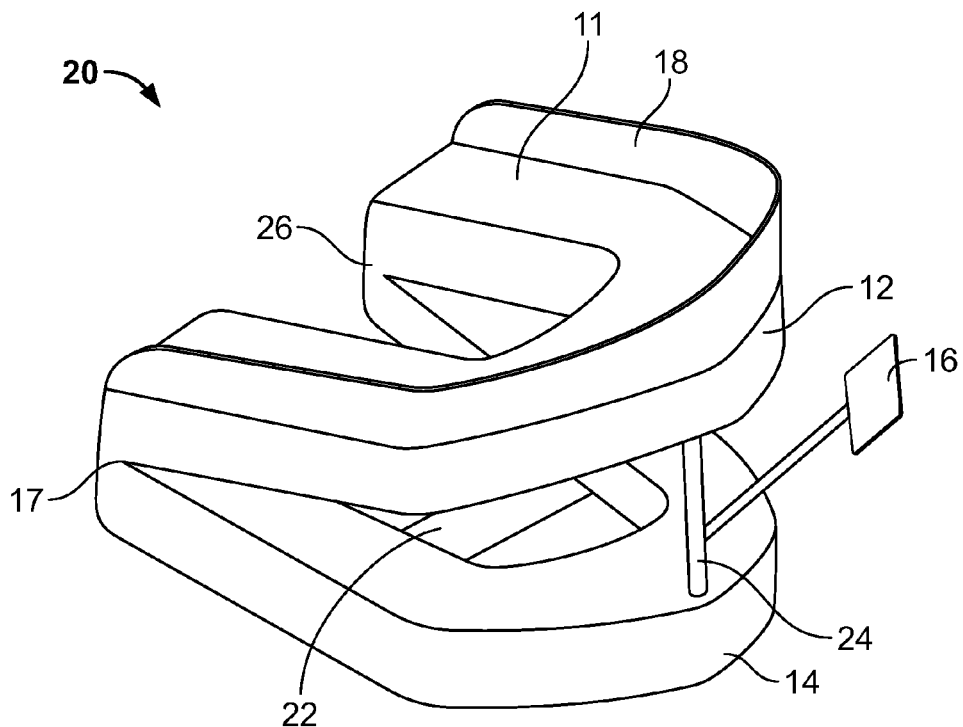

As shown in FIGS. 2A-B, in some cases, an oral stenting device 20 can include an upper tray 12 and a lower tray 14 that can be manufactured as a single piece of flexible material with a common wall 26. Common wall 26 can be a common wall that is one, two, three, five, ten, or more mm in thickness. As oral stenting device 20 is opened from a closed position about a hinge arrangement 17, common wall 26 can flex to accommodate the opening motion. For example, the region of common wall 26 can be composed of a flexible material that can allow opening and closing of oral stenting device 20.

With further reference to FIGS. 2A-B, oral stenting device 20 can include tongue depressor 22. Tongue depressor 22 can be configured to extend from one side of lower tray 14 to the other side of lower tray 14. In some cases, tongue depressor 22 can be configured to depress the user's tongue out of a radiation field. Tongue depressor 22 can be composed of a semi-rigid or rigid plastic, resin, polymer, or other material suitable to stabilize a user's tongue. In some cases, tongue depressor 22 can be part of lower tray 14 as shown in FIG. 2. In some cases, tongue depressor 22 can be part of upper tray 12 such that a normal upright use of the oral stenting device positions the tongue depressor away from the tongue and an inverted use of the oral stenting device positions the tongue depressor in contact with the tongue. In some cases, tongue depressor 22 can be used to elevate the user's tongue. In some cases, upper tray 12 or lower tray 14 can be configured as a solid semi-ellipse such that the user's tongue can be depressed without a separate tongue depressor. In some cases, tongue depressor 22 can be slidably engaged with upper tray 12 or lower tray 14 to allow customizable placement. In some cases, tongue depressor 22 can be removable.

Any appropriate material or combination of materials can be used to make an oral stenting device provided herein or any component of an oral stenting device provided herein (e.g., base member 11). For example, upper tray 12, lower tray 14, actuator 16, teeth guard 18, and base member 11 can be composed of any appropriate material or combination of materials such as, for example, carbon, molded plastics, or polymers. In some cases, an oral stenting device provided herein or a component of an oral stenting device provided herein (e.g., base member 11) can be rigid, semi-rigid, or flexible. In some cases, an oral stenting device provided herein or a component thereof can be capable of being custom molded to the configuration of the user's teeth or mouth. For example, base member 11 (or any component of an oral stenting device) can be composed of a thermoplastic material such that base member 11 can be custom molded by increasing the temperature of the material to a level where the material becomes pliable. Once the material of the base member is pliable, the oral stenting device can be inserted into the user's mouth in a pliable state and allowed to cool, thereby forming a custom configuration for that user. Examples of appropriate thermoplastic materials include, without limitation, ethylene vinyl alcohol, ethylene vinyl acetate, urethane, styrene block copolymer, rubber, polystyrene, polybutadiene, polyisoprene, polyolefin, organopolysiloxane, alicyclic saturated hydrocarbon resin, polycaprolactone, polyethylene, unfilled polycarbonate, ester gum, polyethylenetetraphthalate, terpolymer, nylon, nylon copolymer, polyester, copolyester, or any combination thereof. In some cases, upper tray 12, lower tray 14, and/or teeth guard 18 can be shaped to prevent thermoplastic material from spreading when the oral stenting device is being fitted. In some cases, an oral stenting device provided herein or a component thereof (e.g., a moldable insert capable of forming a custom oral stenting device provided herein) can be made of a light-curable polymer, a non-toxic rubber, plastic, or polymer, or one or more materials described elsewhere (see, e.g., U.S. Pat. Nos. 5,550,383; 5,190,990; and 5,775,900 and U.S. Patent Application Publication Nos. 20090038624; 20090130624; and 20100108078).

In some cases, an oral stenting device provided herein or a component thereof (e.g., upper tray 12, lower tray 14, and teeth guard 18) can be configured to be thick enough to shield the mouth and teeth from backscattering of electrons that occurs when dental materials such as high gold alloy or amalgam are present. For example, upper tray 12, lower tray 14, and teeth guard 18 can be about 2 mm or more (e.g., 3, 4, 5, 6, 7, 8, 9, 10, or more mm) in thickness. In some cases, an oral stenting device provided herein or a component thereof (e.g., upper tray 12, lower tray 14, and teeth guard 18) can be substantially radiolucent or can be substantially radiopaque. In some cases, an oral stenting device provided herein or a component thereof (e.g., upper tray 12, lower tray 14, and teeth guard 18) can be configured to include one or more radiopaque markers or materials to enhance identification on imaging films to verify proper location. In some cases, an oral stenting device provided herein can include a portion of teeth guard 18 or other oral stenting device element that protrudes outside of the user's mouth to further shield the user's lips.

Figure 3:
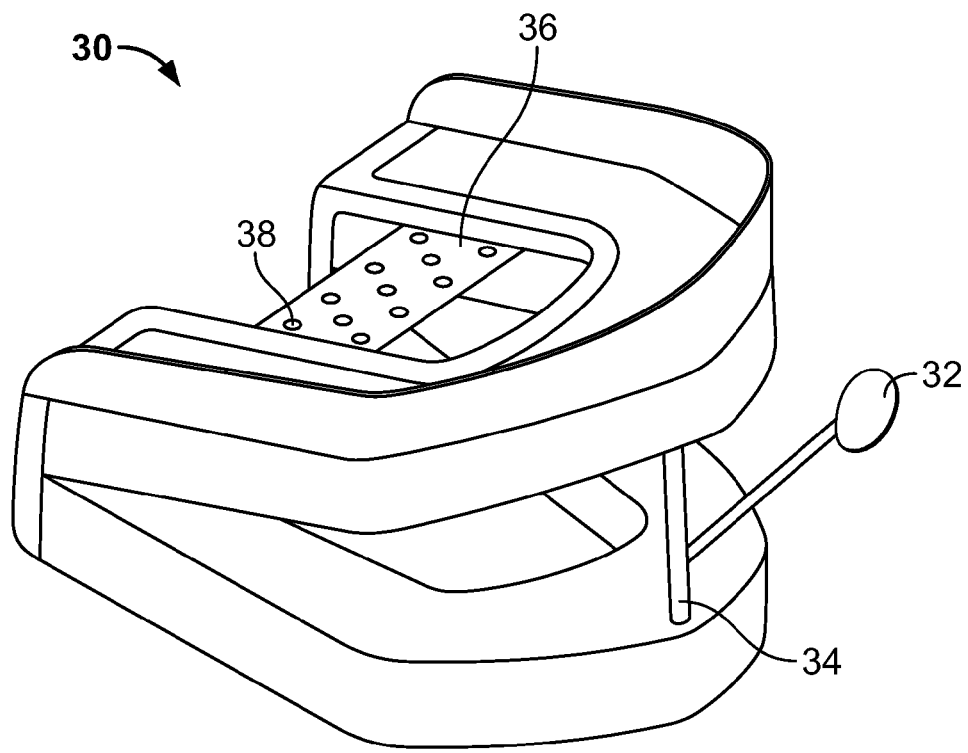
FIG. 3 is a prospective view of an oral stent device in an open position, in accordance with some embodiments.

With further reference to FIGS. 1A-D and 2A-B, actuator 16 can be configured to change the angular relationship between upper tray 12 and lower tray 14 upon actuation, thereby allowing the intraoral stenting device to be positioned in a user's mouth in a lower profile setting (e.g., a closed position) and subsequently be adjusted to a treatment setting (e.g., open position). In some cases, actuator 16 can be configured to include a mechanism 24 (e.g., a ratcheting mechanism, a dial mechanism, a screw mechanism, a lever mechanism, a spring mechanism, a scissor jack mechanism, a telescoping mechanism, or combination thereof) to selectively open an oral stenting device provided herein or to separate upper tray 12 from lower tray 14. For example, as shown in FIG. 3, an oral stenting device 30 can be opened by turning a dial 32 in, for example, a clockwise direction to the desired position and closed by turning dial 32 in, for example, a counterclockwise direction via a dial mechanism 34. Dial mechanism 34 can include a threaded rod to control the degree of separation between upper tray 12 and lower tray 14. In some cases, an oral stenting device provided herein can include incremental markers or position indicators that allow repeat treatment sessions to occur with the same angular relationship between upper tray 12 and lower tray 14.

An actuator and opening mechanism of an oral stenting device provided herein can be located in any appropriate position along the upper tray or lower tray. For example, an actuator and opening mechanism can be located at the center line of the oral stenting device (e.g., in alignment with a user's nose). In some cases, an actuator and opening mechanism can be located to the left or right of such a center line. For example, an actuator and opening mechanism can be located one, two, three, or more cm to the left or right of the center line of an oral stenting device. In some cases, an actuator and opening mechanism of an oral stenting device provided herein can be located on a track of the upper tray and lower tray such that the actuator and opening mechanism can be moved (e.g., slidably moved) from one position (e.g., the center line) to another position (e.g., three cm to the right of the center line). In such cases, the opening mechanism can include a locking element configured to hold the opening mechanism in a desired position along the oral stenting device.

Figure 4:
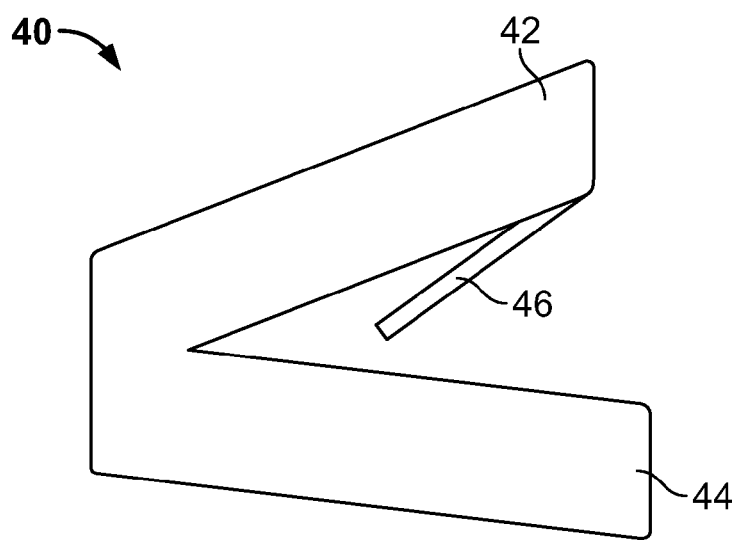
FIG. 4 is a side view of an oral stent device, in accordance with some embodiments.

As shown in FIG. 3, oral stenting device 30 can include a tongue depressor 36 that can include one or more pores 38 or other openings. Tongue depressor 36 can include any appropriate number of pores. For example, tongue depressor 36 can include one, two, three, four, five, six, seven, eight, nine, ten, 11, 15, 20, 25, or more pores. As shown in FIG. 4, an oral stenting device 40 can include an upper tray 42, a lower tray 44, and a tongue depressor 46. Tongue depressor 46 can be configured to extend at a downward angle from upper tray 42.

Figure 5A:
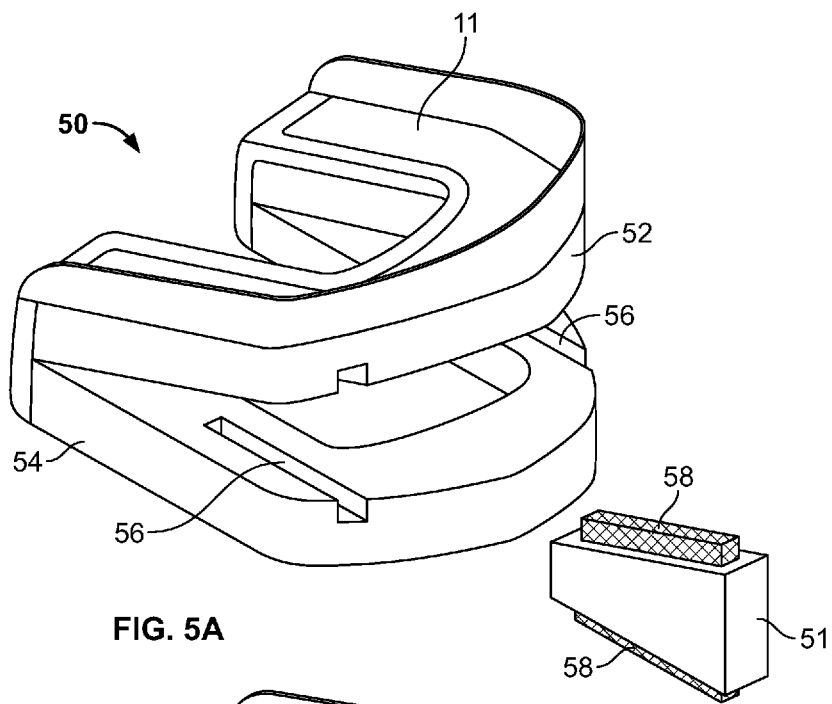
FIGS. 5A-B are prospective views of an oral stent device in a position with (FIG. 5B) and without (FIG. 5A) an inserted wedge device, in accordance with some embodiments.
Figure 5B:
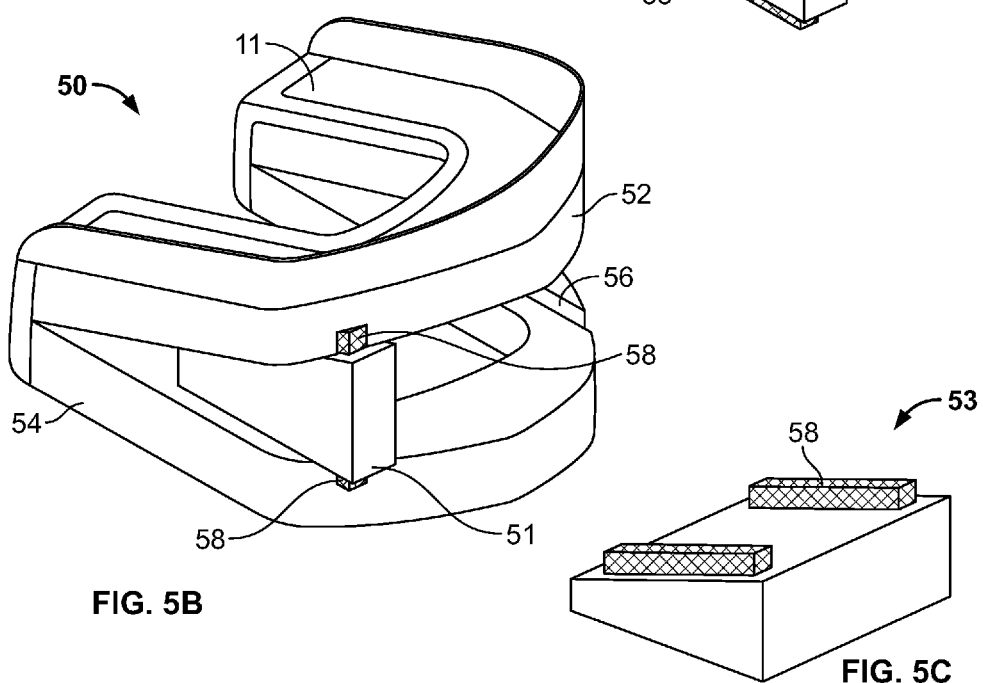
Figure 5C:
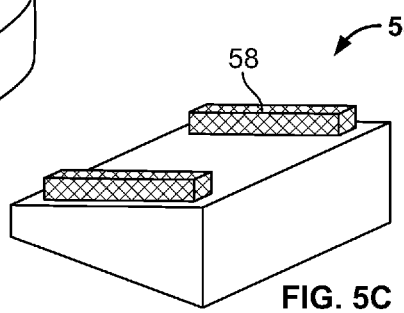
FIG. 5C is a prospective view of a wedge device, in accordance with some embodiments.

With reference to FIGS. 5A-B, an oral stenting device 50 can be configured to receive one or more removable wedges 51. In such cases, oral stenting device 50 can include an upper tray 52 and a lower tray 54. Upper tray 52 and lower tray 54 can include grooves 56. Grooves 56 can be configured to releasably and slidably mate with extension elements 58 of wedge 51. Upon insertion of wedge 51, upper tray 52 can be separated from lower tray 54. In some cases, upper tray 52 and lower tray 54 can include extension elements, in which cases wedge 51 can be configured to include corresponding grooves. In some cases, a wedge 53 can be used as shown in FIG. 5C. Wedge 53 can include two extension elements 58 on its top surface and two extension elements 58 on its bottom surface such that it can releasably and slidably mate with the grooves of oral stenting device 50.

Figure 6A:
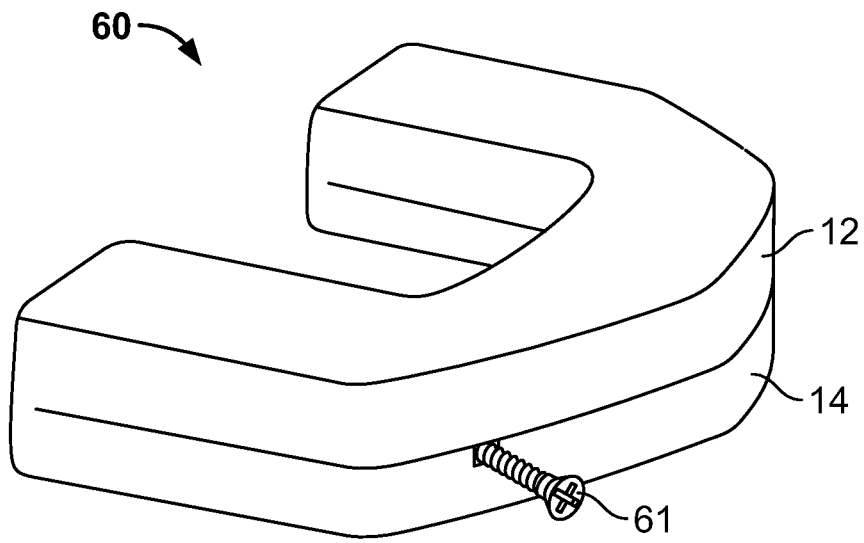
FIGS. 6A-B are prospective views of an oral stent device in a closed position (FIG. 6A) and an open position (FIG. 6B), in accordance with some embodiments.
Figure 6B:
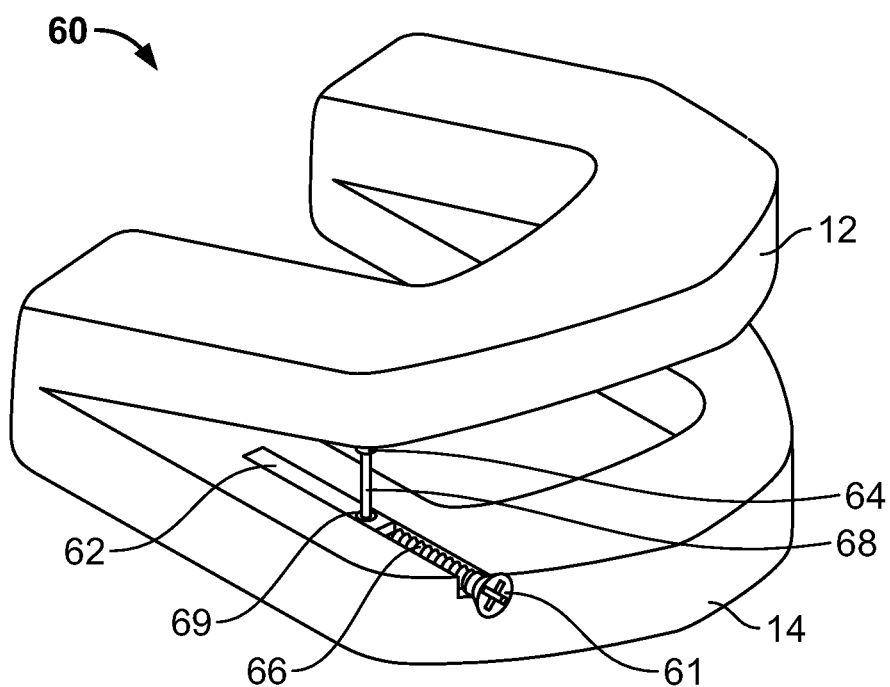

With reference to FIGS. 6A-B, an oral stenting device 60 can include a lever mechanism 61 (e.g., a type 1 lever mechanism). In such cases, lever mechanism 61 can include a screw mechanism 66 that can engage a bar 68 at fulcrum point 69. Screw mechanism 66 can include a housing (e.g., a fixed housing) and a screw element. The housing can be integral to lower tray 14 or a separate component attached to an upper surface of lower tray 14. Bar 68 can be attached at attachment point 64. Attachment point 64 can include a mechanism (e.g., a ball and socket, hinge, etc.) to allow angular movement of bar 68. Fulcrum point 70 can include a mechanism (e.g., ball and socket, hinge, etc.) to allow bar 68 to move along track 62 in a fore-aft motion when actuated by lever mechanism 61. Rotation of lever mechanism 61 can cause screw mechanism 66 to move fulcrum point 70 such that the angular relationship of upper tray 12 and lower tray 14 is changed. When oral stenting device 60 is fully closed (FIG. 6A), bar 68 can be substantially parallel to upper tray 12 and lower tray 14. As shown in FIG. 6B, bar 68 can be sufficiently perpendicular to upper tray 12 and lower tray 14 to position oral stenting device 60 in an open position. In some cases, the entire lever mechanism could be inverted such that attachment point 64 can be part of lower tray 14, and track 62, screw mechanism 66, and fulcrum point 70 can be part of upper tray 12.

Figure 7A:
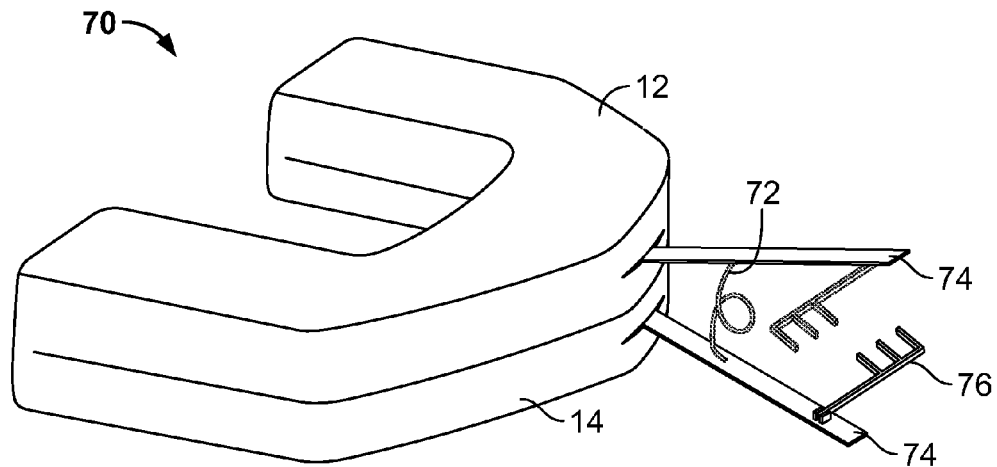
FIGS. 7A-B are prospective views of an oral stent device in a closed position (FIG. 7A) and an open position (FIG. 7B), in accordance with some embodiments.
Figure 7B:
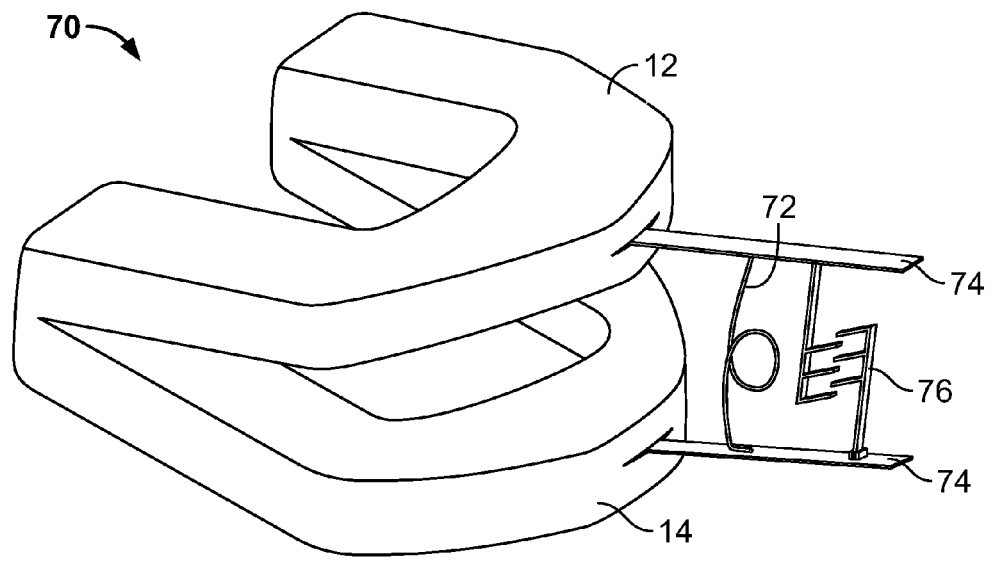

With reference to FIGS. 7A-B, an oral stenting device 70 can include a spring mechanism 72 (e.g., a coil spring, a compression spring, a torsion spring, a spring clip, etc.). In such cases, spring mechanism 72 can be actuated by actuators 74. In some cases, oral stenting device 70 can include locking elements 76. For example, oral stenting device 70 can be opened by squeezing actuators 74 to engage locking elements 76 and fix spring mechanism 72 in a desired position (FIG. 7B). In some cases, locking elements 76 can include incremental markers or position indicators to allow repeat sessions to occur with the same angular relationship between upper tray 12 and lower tray 14. In some cases, spring mechanism 72 can be located outside the mouth when oral stenting device 70 is in use. In some cases, spring mechanism 72 can be located inside the mouth when oral stenting device 70 is in use, with actuators 74 accessible outside of the mouth. In some cases, spring mechanism 72 can be configured such that locking elements 76 are engaged while oral stenting device 70 is in a closed position.

Figure 8:
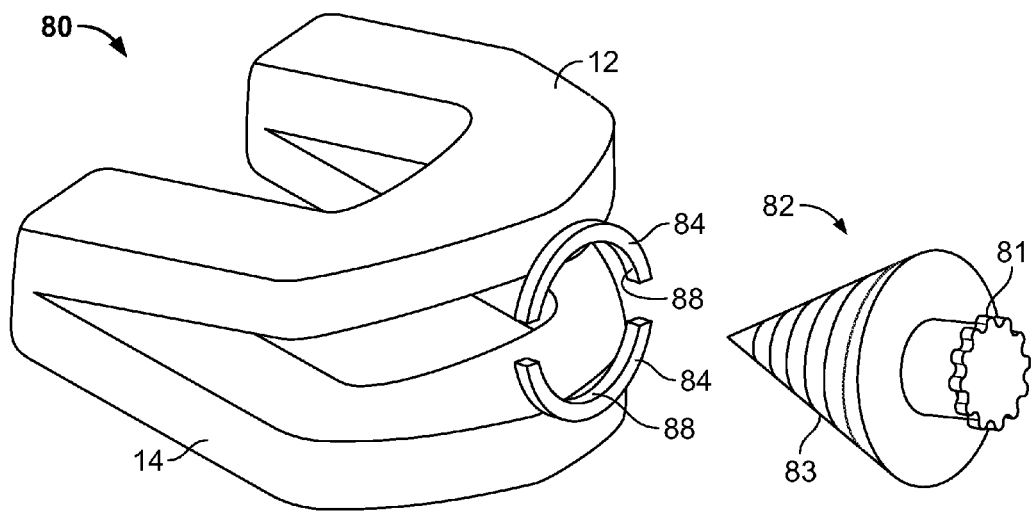
FIG. 8 is a prospective view of an oral stent device, in accordance with some embodiments.

With reference to FIG. 8, an oral stenting device 80 can be configured to receive a screw device 82. In some cases, screw device 82 can be tapered or wedge-shaped. For example, insertion of screw device 82 can cause oral stenting device 80 to be configured in an open position. In some cases, screw device 82 can engage guide elements 84. In some cases, guide elements 84 can include a threaded surface 88 to receive screw device 82. In some cases, guide elements 84 can include partial (e.g., semi-circular) or full diameter (e.g., circular, oval, elliptical, etc.) threaded surface 88.

With further reference to FIG. 8, screw device 82 can include a gripping region 81 and a threaded region 83. Gripping region 81 can be configured to allow a physician or other medical personnel to hold and insert screw device 82 into oral stenting device 80 via a twisting motion. Threaded region 83 can be configured to mate with threaded surface 88.

Figure 9:
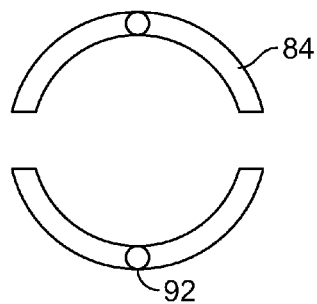
FIG. 9 is a top view of a guide element, in accordance with some embodiments.

With reference to FIG. 9, in some cases, guide elements 84 can include an adjustable diameter. In some cases, guide elements 84 can optionally include a flexible joint 92 (e.g., a hinge mechanism). In some cases, guide elements 84 can be fixedly attached to any surface of upper tray 12, lower tray 14, or any other component of oral stenting device 80. In some cases, screw mechanism 82 can include incremental markers or position indicators to allow repeat sessions to occur with the same angular relationship between upper tray 12 and lower tray 14. In some cases, screw mechanism 82 can optionally include a tether (e.g., a suture line, string, etc.) attached to oral stenting device 80 so that screw mechanism 82 remains in close proximity to oral stenting device 80 between treatment sessions.

An oral stenting device provided herein can be custom molded to fit by any standard technique (e.g., boil and bite, etc). For example, an oral stenting device provided herein can be placed in heated water until it becomes pliable. The closed stent may then be placed into a user's mouth, allowing a base member to assume a custom conformation and allowed to cool until stable.

During use, an oral stenting device provided herein can be placed in a user's mouth (e.g., a patient's mouth) in a closed position. An actuator then can be used to open the oral stenting device, placing the user's mouth in a position as required for treatment. Upon completion of a treatment session, an actuator can be used to close the oral stenting device for easy removal. The position of the open oral stenting device can be reproduced in subsequent treatments by use of indictor marks which can be included as part of an actuator mechanism or the oral stenting device.

In some cases, an oral stenting device provided herein can be configured as a component of a kit. For example, such a kit can include one or more actuators, one or more upper trays, one or more lower trays, and one or more base members of the same or different sizes (e.g., small, medium, large, etc). In some cases, the actuators can be wedges or screw mechanisms in a plurality of sizes. In some cases, the one or more actuators, one or more upper trays, one or more lower trays, and one or more base members can be packaged together in a sterile condition such as in a sealed container. In some cases, the kits provided herein can include instructional materials.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for using an oral stenting device during radiation therapy, wherein said method comprises:
    (a) inserting an oral stenting device into a mouth of a human patient, wherein said oral stenting device comprises an upper tray, a lower tray, an actuator, a tongue depressor, and a locking element, wherein said actuator is operable to change an angular relationship between said upper tray and said lower tray to open said mouth, and wherein said locking element is configured to lock said mouth in an open position,
    (b) actuating said actuator to change said angular relationship to position said mouth in said open position,
    (c) locking said locking element to lock said mouth in said open position,
    (d) performing radiation therapy on a head or neck region of said human patient,
    (e) unlocking said locking element to release said mouth from said open position,
    (f) actuating said actuator to change said angular relationship to move said mouth from said open position toward a closed position, and
    (g) removing said oral stenting device from said mouth.

2. The method of claim 1, wherein said oral stenting device further comprises a base member.

3. The method of claim 2, wherein said base member comprises a thermoplastic material.

4. The method of claim 1, wherein said actuator comprises a ratcheting mechanism.

5. The method of claim 1, wherein said tongue depressor is slidably engaged with said lower tray.

6. The method of claim 1, wherein said oral stenting device comprises a thermoplastic material.

7. The method of claim 1, wherein said oral stenting device comprises a teeth guard structure that extends upward from said upper tray along an outside edge of said upper tray.

8. The method of claim 1, wherein said oral stenting device comprises a teeth guard structure that extends downward from said lower tray along an outside edge of said lower tray.

9. The method of claim 1, wherein said oral stenting device comprises an upper teeth guard structure that extends upward from said upper tray along an outside edge of said upper tray and a lower teeth guard structure that extends downward from said lower tray along an outside edge of said lower tray.

10. The method of claim 1, wherein said oral stenting device comprises a hinge connecting said upper tray to said lower tray.

\* \* \* \* \*